(12) United States Patent
Dmuschewsky

(10) Patent No.: US 9,572,554 B2
(45) Date of Patent: Feb. 21, 2017

(54) SURGICAL SLIDING SHAFT INSTRUMENT THAT CAN BE DISMANTLED

(71) Applicant: WALDEMAR LINK GmbH & Co. KG, Hamburg (DE)

(72) Inventor: Klaus Dmuschewsky, Hamburg (DE)

(73) Assignee: WALDEMAR LINK GMBH & CO. KG, Hamburg (DE)

( * ) Notice: Subject to any disclaimer, the term of this patent is extended or adjusted under 35 U.S.C. 154(b) by 389 days.

(21) Appl. No.: 14/378,299

(22) PCT Filed: Jan. 31, 2013

(86) PCT No.: PCT/EP2013/051941
§ 371 (c)(1),
(2) Date: Aug. 12, 2014

(87) PCT Pub. No.: WO2013/120701
PCT Pub. Date: Aug. 22, 2013

(65) Prior Publication Data
US 2015/0005749 A1    Jan. 1, 2015

(30) Foreign Application Priority Data

Feb. 13, 2012  (DE) .................... 20 2012 001 348 U

(51) Int. Cl.
*A61B 17/00*  (2006.01)
*A61B 17/16*  (2006.01)

(52) U.S. Cl.
CPC ........... *A61B 17/00* (2013.01); *A61B 17/1608* (2013.01); *A61B 17/1611* (2013.01);
(Continued)

(58) Field of Classification Search
CPC ................. A61B 2017/00367; A61B 2218/00;
A61B 2090/0813; A61B 17/00; A61B 17/1608; A61B 17/1611
See application file for complete search history.

(56) References Cited

U.S. PATENT DOCUMENTS 6,126,674 A    10/2000  Janzen
2002/0151931 A1  10/2002  Tontarra
(Continued)

FOREIGN PATENT DOCUMENTS

DE    197 48 369     5/1999
DE    201 03 630    10/2001
(Continued)

OTHER PUBLICATIONS

International Search Report and Written Opinion dated Jul. 19, 2013, directed to International Application No. PCT/EP2013/051941; 18 pages.

*Primary Examiner* — Gary Jackson
*Assistant Examiner* — Scott T Luan
(74) *Attorney, Agent, or Firm* — Morrison & Foerster LLP

(57) ABSTRACT

A dismantlable surgical sliding shaft instrument having a function shaft comprising a guide element, a slide element supported on the guide element in a sliding manner and having a coupling element, an undercut rail oriented along the sliding direction of the slide element and having a mounting opening at the proximal end of the rail, a profile web having a profile complementary to the rail, a gripping part having a rear gripping element at an angle at the end of the guide element, a front gripping element pivotably supported on the guide element and having a carrier element to carry along the coupling element, and a securing device on the rear gripping element and engaging with a form closure component in the proximal part of the guide groove in a securing position, and a transition piece complementary to
(Continued)

the form closure component between the distal part and the proximal part.

10 Claims, 5 Drawing Sheets

(52) U.S. Cl.
CPC ............... *A61B 2017/00367* (2013.01); *A61B 2090/0813* (2016.02); *A61B 2218/00* (2013.01)

(56) References Cited

U.S. PATENT DOCUMENTS

| | | |
|---|---|---|
| 2003/0088268 A1 | 5/2003 | Weinmann |
| 2004/0073232 A1 | 4/2004 | Widmann |
| 2011/0046661 A1* | 2/2011 | Kuehn ............... A61B 17/1608 606/206 |

FOREIGN PATENT DOCUMENTS

| | | |
|---|---|---|
| DE | 20 2008 001 675 | 5/2008 |
| DE | 10 2008 034287 | 2/2010 |
| EP | 0 706 780 | 4/1996 |
| EP | 1 212 983 | 6/2002 |
| EP | 1 491 155 | 12/2004 |

* cited by examiner

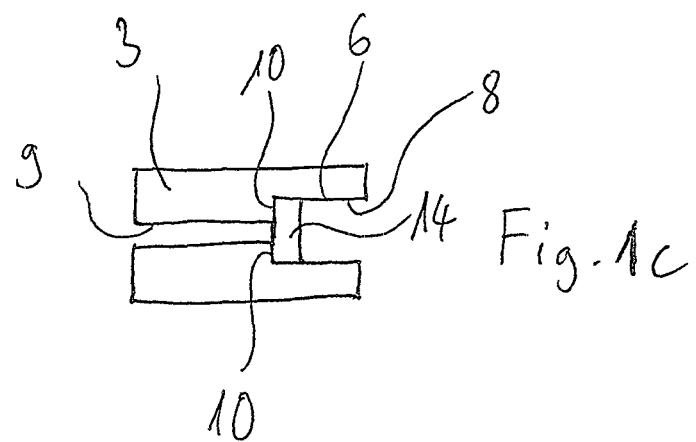
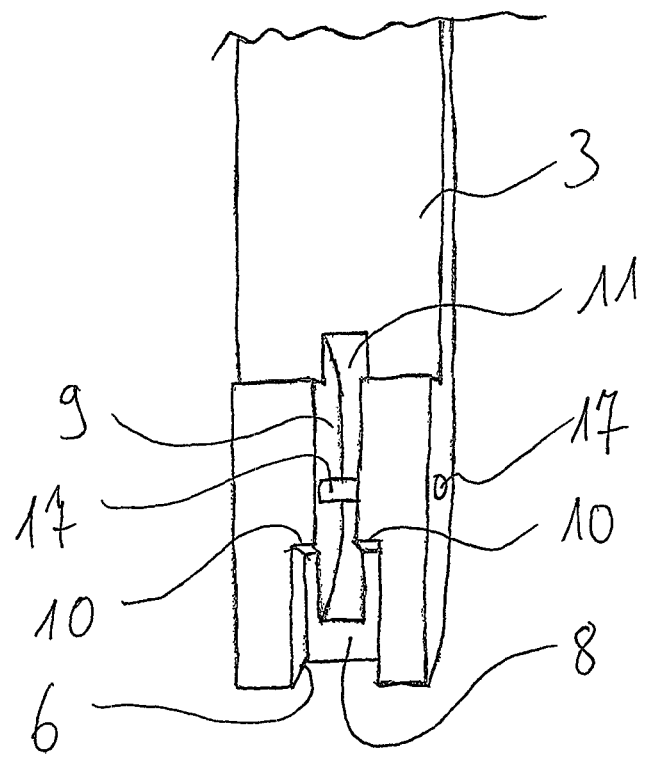

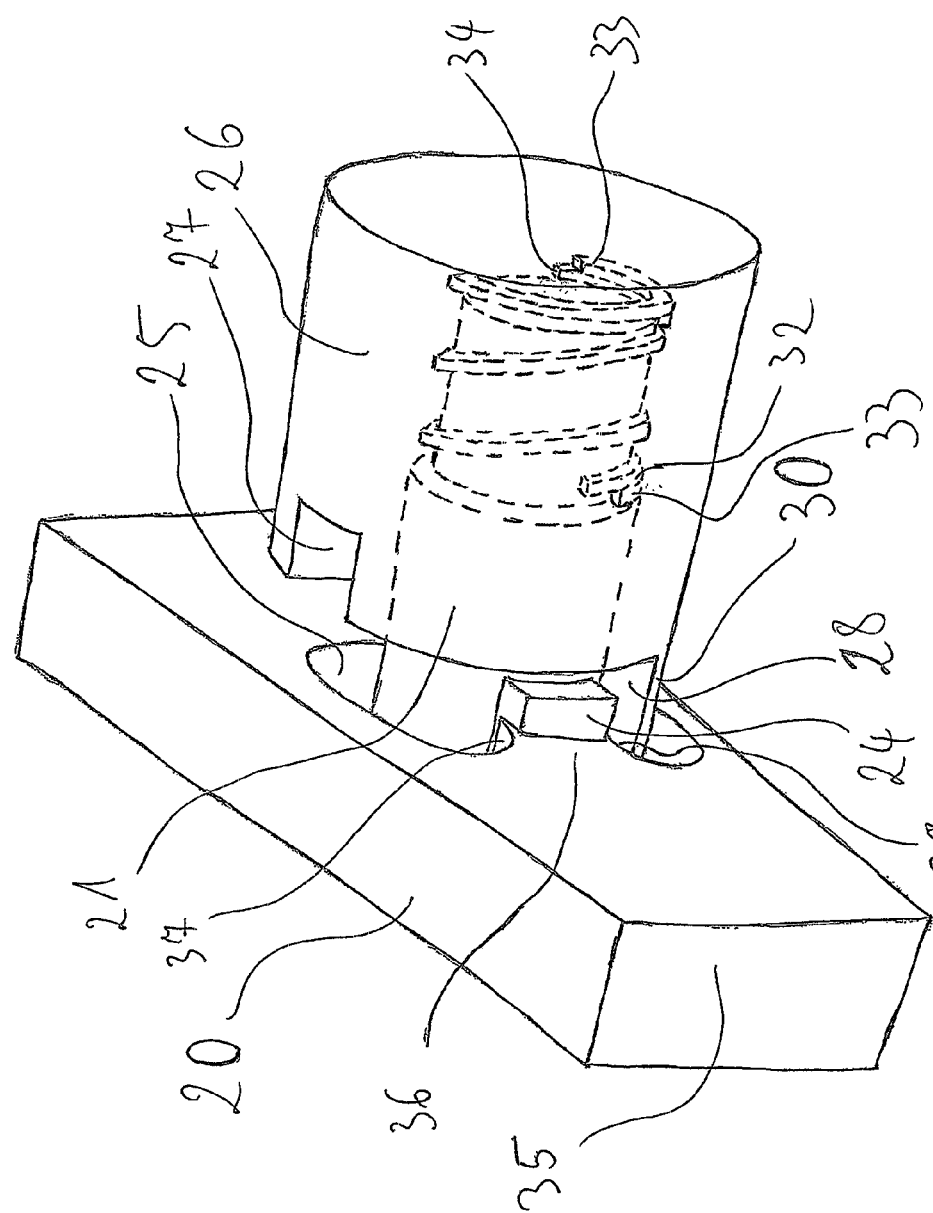

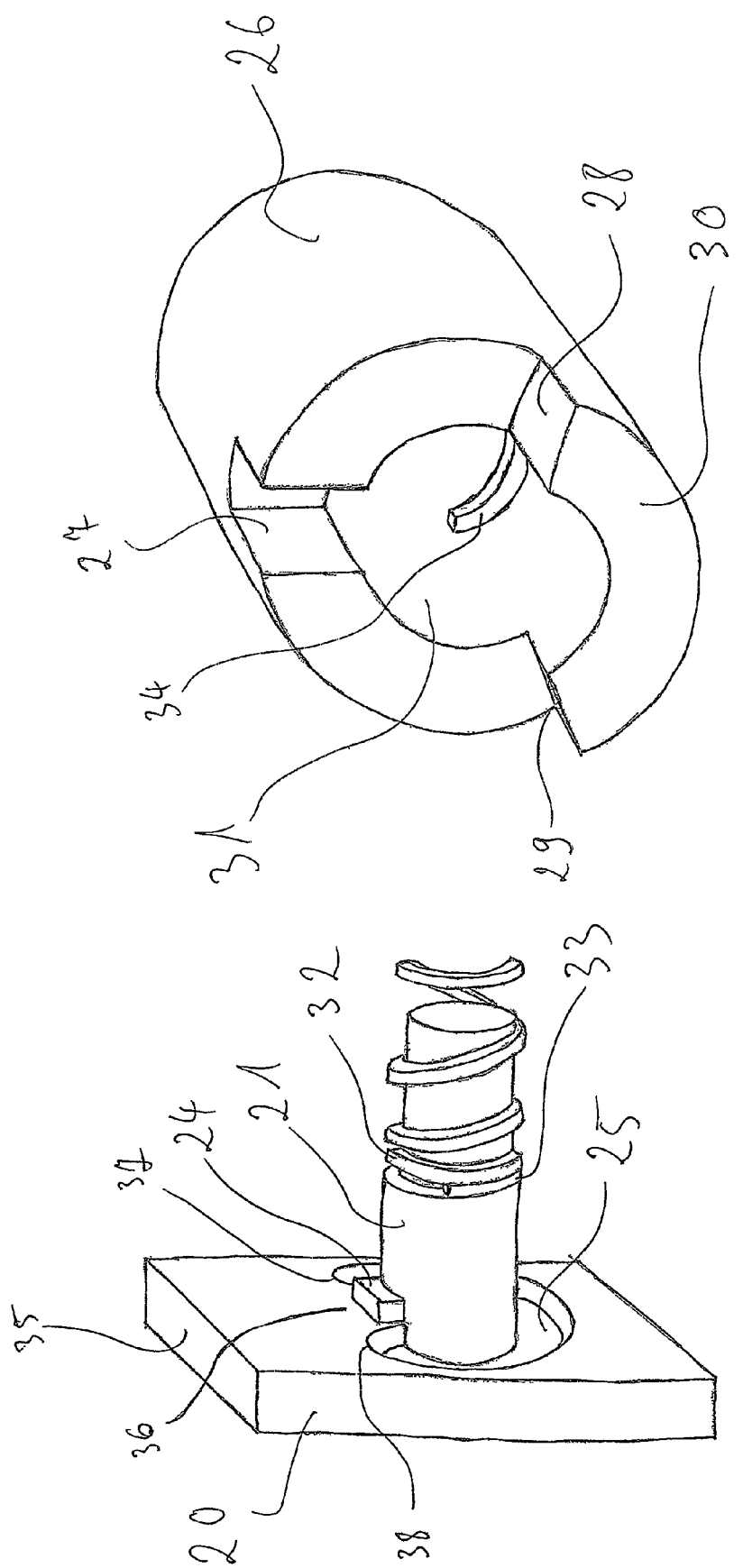

SURGICAL SLIDING SHAFT INSTRUMENT THAT CAN BE DISMANTLED

REFERENCE TO RELATED APPLICATIONS

This application is a national stage application under 35 USC 371 of International Application No. PCT/EP2013/051941, filed Jan. 31, 2013, which claims priority to German Application No. 20 2012 001 348.3, filed Feb. 13, 2012, the entire contents of which are incorporated herein by reference.

FIELD OF THE INVENTION

The invention relates to the locking mechanism of a dismantlable surgical sliding shaft instrument.

BACKGROUND OF THE INVENTION

Surgical instruments, in particular surgical sliding shaft instruments, have to be cleaned after each use. In doing so, it is also necessary to clean surfaces that are arranged between different components of the instruments. For this purpose, the instruments are designed such that they can be dismantled into several parts. The instrument has, on a guide element, a rail that is oriented along a slide element and that has a proximal part and a distal part. The distal part of the rail has an undercut profile. The proximal part of the rail has a mounting opening. Moreover, the sliding shaft instrument has a slide element, which comprises a profile web with a profile matching the rail profile. The profile web engages in the rail. The slide element, which is arranged slidably on a guide element, can be released from the guide element as a result of the dismantling, such that the slide surfaces can be cleaned. The slide element with the profile web is pushed to the proximal end of the rail, such that the profile web is arranged in the mounting opening, from which it can be released from the rail. To prevent dismantling during a surgical intervention, a locking mechanism is provided.

It is known from DE 20 2008 001 675 U1 to initiate the dismantling of the sliding shaft instrument by moving two grip parts wide open. For this purpose, a slide element, which is mounted slidably on a guide element, has a guide groove at its proximal end, said guide groove being composed of two parts. The guide groove is oriented in the direction of movement of the slide element. The distal part of the guide groove is narrower than the proximal part of the guide groove. Moreover, the guide element has, at its proximal end, a locking slide, which engages in the proximal part of the guide groove. The transition between the proximal part and the distal part of the guide groove is rounded by radii. By means of the transition, the slide element is stopped by the locking slide during the opening of the grips of the sliding shaft instrument, such that a dismantling of the sliding shaft instrument is prevented.

DE 197 48 369 C2 relates to a dismantlable sliding shaft instrument which has, as locking mechanism, a rotation safety element. The rotation safety element is designed as a rotatably mounted disk. The disk is arranged at the proximal end of the guide element such that it blocks the path of the slide element. The disk has a recess which, for unlocking purposes, is rotated to the slide element. The blocking of the slide element is thereby canceled. Moreover, the locking element can also be arranged on the movable grip part of the sliding shaft instrument. In this case, the locking mechanism blocks the opening of the second grip part by form-fit engagement with the underside of the guide element.

The abovementioned locking mechanisms have in common the disadvantage that they are unable to guarantee secure locking. Thus, when the locking mechanism is designed as a slide, a bending of the locking slide can be caused by the guide groove rounded with radii. Moreover, the locking slide may be bent by forcible opening of the grip elements of the sliding shaft instrument, such that an inadvertent dismantling of the sliding shaft instrument may occur in both cases. In the embodiment with the rotation safety element, accidental opening may be caused by the free rotatability of the safety means. Therefore, in this embodiment too, an inadvertent dismantling may occur during a surgical intervention.

It is also known to equip the rotation safety element with a locking element. The locking element is arranged on a pin stub, which is coupled to a bushing arranged on the grip part. The pin stub is mounted movably in its axial direction. The bushing also has a recess, into which the locking element is placed when securing the slide element. A disadvantage of this device is that the rotation safety element can cause a locking of the slide element in different positions. However, secure locking is ensured only in a position in which the locking element is arranged in the recess of the bushing. Consequently, incorrect positioning of the rotation safety element can lead to accidental dismantling of the sliding shaft instrument.

SUMMARY OF THE INVENTION

An object of the invention is to prevent the dismantlable sliding shaft instrument from being opened too wide and in so doing to ensure secure locking of the dismantling mechanism.

This can be achieved by the subjects as broadly disclosed herein. Advantageous developments relate to the detailed embodiments below.

A first alternative of the invention comprises a dismantlable surgical sliding shaft instrument comprising a function shaft, which has a guide element and a slide element mounted slidably on the guide element and has a coupling element, and comprising an undercut rail, which is oriented along the sliding direction of the slide element and has a mounting opening, and a profile web with a profile that matches the rail, a grip part, which has a rear grip element arranged at an angle on the end of the guide element, and a front grip element mounted pivotably on the guide element, which front grip element has a carrier element designed to carry along the coupling element, and a safety device arranged on the rear grip element, which safety device engages with a form-fit component in the proximal part of the guide groove in a safety position. A transition piece matching the form-fit component is arranged between the distal part and the proximal part.

In a second alternative, the invention further comprises a dismantlable surgical sliding shaft instrument, comprising a function shaft, which has a guide element and a slide element mounted slidably on the guide element and has a coupling element, and comprising an undercut rail, which is oriented along the sliding direction of the slide element and has a mounting opening, and a profile web with a profile that matches the rail, a grip part, which has a rear grip element arranged at an angle on the end of the guide element, and a front grip element mounted pivotably on the guide element, which front grip element has a carrier element designed to carry along the coupling element, and a rotation safety element which is mounted on a rotatable pin stub and has a locking component, wherein the pin stub is mounted in a bushing secured in a rotationally fixed manner on the grip, wherein the rotation safety element is arranged with a form fit on the function shaft in a safety position. The bushing has an edge with a first form-fit surface, and the rotation safety element has a recess with a second form-fit surface, wherein the edge engages in the recess, and wherein the second form-fit surface is arranged on the first form-fit surface in an opening position of the rotation safety element.

A basic concept of the invention is that an incredibly effective increase in the locking safety is achieved by means of a design measure.

In the first alternative, the matching transition piece provides an abutment surface for the form-fit component of the safety device. The abutment surface has the effect that the freedom of movement of the form-fit component is limited in the safety position. Bending and displacement of the safety device is effectively prevented by the limited freedom of movement.

In the second alternative, the invention limits the freedom of movement of the rotation safety element. The rotation of the rotation safety element is limited by means of a design measure. The edge of the bushing with the first form-fit surface engaging in the recess of the rotation safety element impacts the form-fit surface of the bushing during a rotation, such that a further rotation of the rotation safety element is not possible because of the form-fit engagement of the form-fit surfaces. In this way, the rotation safety element can no longer cause the slide element to be locked in the incorrect position. This increases the locking safety of the instrument and the maneuvering during the operation.

Thus, in both alternative embodiments of the invention, an effective increase in the locking safety is achieved by an incredibly simple design measure. For a surgeon using the dismantlable sliding shaft instrument there is now no longer any possibility of its being inadvertently dismantled. The invention thus achieves increased safety in handling.

Some of the terms used are explained below:

A safety position is understood as a position of the safety device, or of the rotation safety element, by which the opening angle of the grip elements of the instrument is limited in such a way that dismantling of the instrument is not possible. That is to say, the profile web engaging in the rail is not arranged in the mounting opening when the grip elements are opened to the maximum extent.

An opening position is understood as a position of the safety device, or of the rotation safety element, by which a dismantling of the instrument is possible. The profile web is thus arranged in the mounting opening when the grip parts are opened to the maximum extent.

The proximal end of a component of the sliding shaft instrument signifies the end which is arranged closer to the grip than the opposite end of the component. The distal end of a component designates the end which is closer to the jaw of the instrument, or farther away from the grips, than the opposite end of the component.

The form-fit component and the transition piece are advantageously at a right angle. The right-angled arrangement means that the form fit is perpendicular to the direction of force or of movement of the slide element. Twisting or bending of the safety device is prevented in this way.

In another advantageous embodiment, the transition piece is integral with the slide element.

The safety device advantageously has a restoring spring. The spring presses the safety device into the safety position. Without force acting on it, the safety device thus remains in the safety position. The possibility of remaining accidentally in the opening position is prevented by the restoring spring.

The edge of the bushing advantageously has a third form-fit surface and the recess of the rotation safety element has a fourth form-fit surface. In a further open position, the rotation safety element is arranged with the fourth form-fit surface on the third form-fit surface. This permits more flexible handling of the rotation safety element, since it is now permitted to freely select the direction of rotation of the rotation safety element for unlocking.

Moreover, the first form-fit surface can advantageously be arranged mirror-symmetrically with respect to the third form-fit surface, and the second form-fit surface can be arranged mirror-symmetrically with respect to the fourth form-fit surface.

The form-fit surfaces are advantageously arranged such that the rotation safety element can be rotated only through 90° from the safety position.

In another advantageous embodiment, the pin stub is axially displaceable. Moreover, in this embodiment, the bushing has a recess matching the locking component, wherein the locking component, in the safety position of the rotation safety element, is arranged in the recess of the bushing. A latching, and therefore a precisely defined safety position of the rotation safety element, is thus achieved. Furthermore, a simple rotation of the rotation safety element is no longer possible. Instead, the rotation safety element has to be moved along the pin stub such that the locking component is removed from the recess of the bushing.

Moreover, the axially displaceable pin stub is coupled to the bushing by means of a restoring spring. The restoring spring pulls the pin stub in the direction of the bushing. In this way, the latched rotation safety element cannot independently unlock itself from the safety position. To unlock it, a force has to be applied by the user. This further increases the locking safety.

BRIEF DESCRIPTION OF THE DRAWINGS

The invention is described on the basis of an illustrative embodiment and with reference to the attached drawings, in which:

FIGS. 1a, 1b and 1c each show a schematic view of a surgical sliding shaft instrument with a safety device arranged on the rear grip part, FIG. 1a specifically showing the assembled state, FIG. 1b showing the disassembled state, and FIG. 1c showing a section through the line X;

FIG. 2 shows a schematic view of the proximal part of the slide element from underneath;

FIGS. 4a, 4b and 4c each show a schematic view of the rotation safety means, FIG. 4a specifically showing the rotation safety means with bushing, FIG. 4b showing the rotation safety means with restoring spring, and FIG. 4c showing the bushing.

DETAILED DESCRIPTION OF THE INVENTION

Figure 1A:
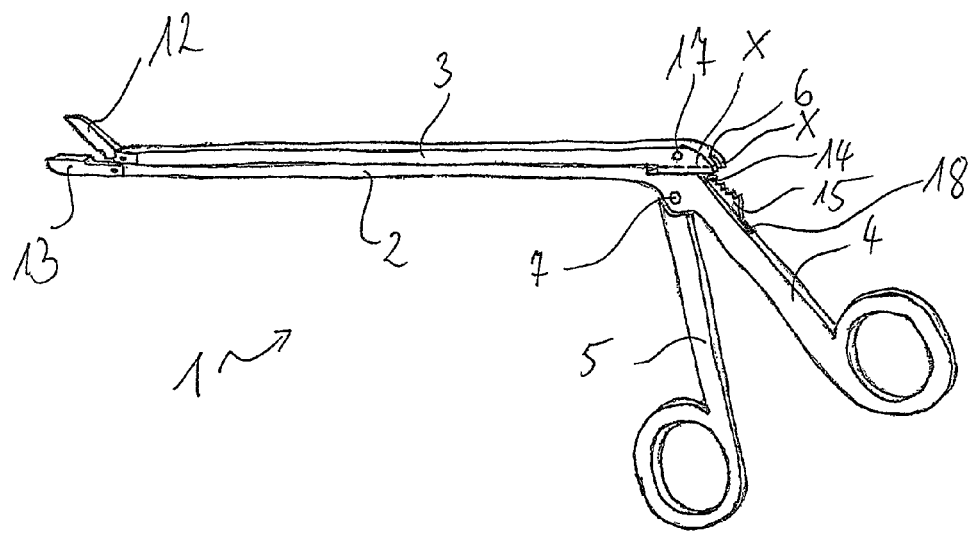
Figure 1B:
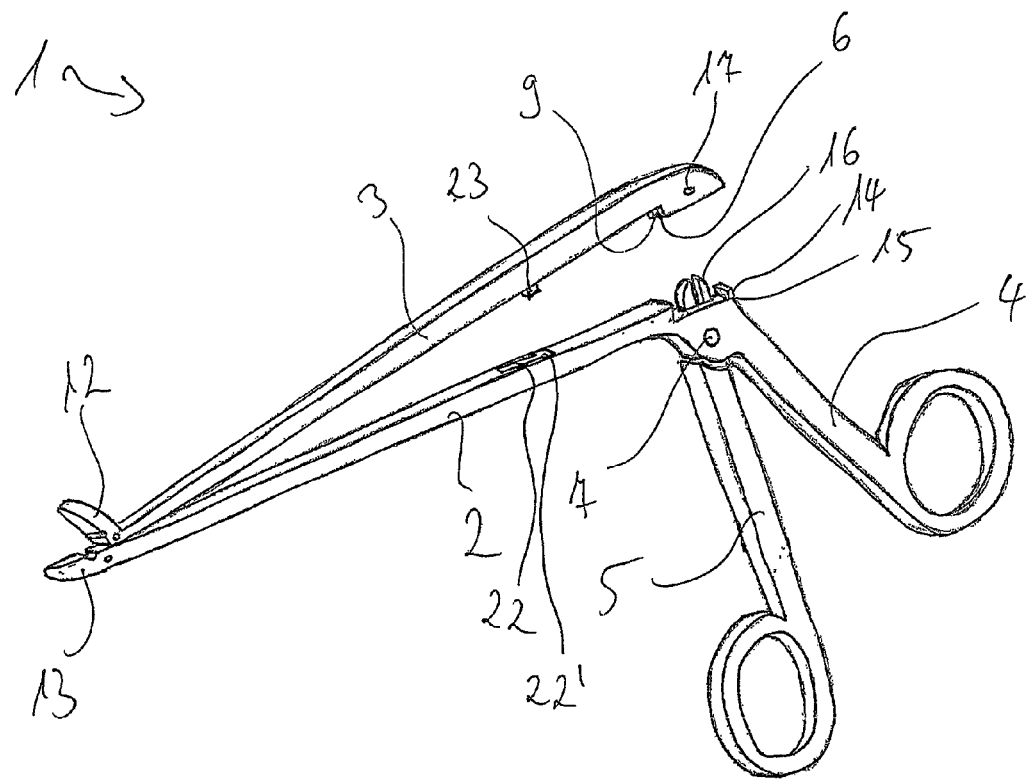
Figure 3:
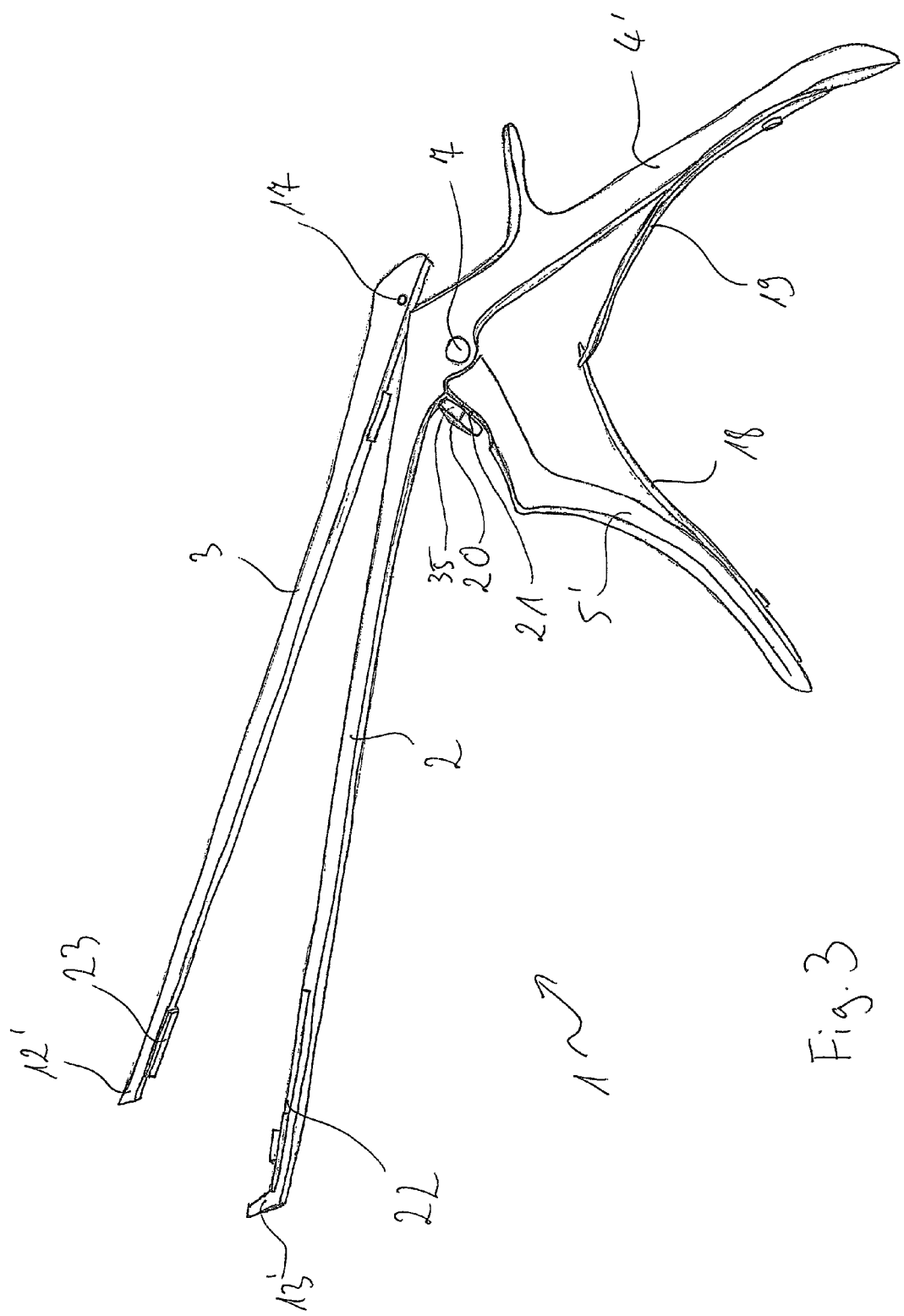
FIG. 3 shows a schematic view of a surgical sliding shaft instrument with a rotation safety means on the front grip part.

The dismantlable surgical sliding shaft instrument is designated in its entirety by reference number 1. It has a function shaft 2, 3, which has a guide element 2 and a slide element 3. Moreover, the instrument 1 has a grip part 4, 5. The grip part 4, 5 comprises a front grip element 5 and a rear grip element 4. The rear grip element 4 is arranged at an angle on the proximal end of the guide element 2. Moreover, the slide element 3 is arranged slidably on the guide element 2. The front grip element 5 is mounted pivotably on the guide element 2 via a hinge element 7 and has carriers 16. At the distal end, the sliding shaft instrument 1 has jaw elements 12, 13. Moreover, the function shaft 2, 3 has a profile web 23 and a two-part undercut rail 22. At its proximal end, the latter has a mounting opening 22', through which the profile web 23 can be pushed into the rail 22 when the grip part 4, 5 reaches its greatest opening angle in a safety position. The profile web 23 has a profile designed to match the undercut profile of the rail 22. When the profile web 23 is pushed into the rail 22, the slide element 3 can no longer be lifted from the guide element 2.

In a first embodiment of the invention, a safety device 15, which comprises a form-fit component 14, is arranged on the rear grip element 4.

Moreover, the slide element 3 has, at its proximal end, a guide groove 6. The guide groove 6 is divided into a proximal part 8 and a distal part 9. The proximal part 8 is broader than the distal part 9. A transition piece 10 is arranged between the proximal part 8 and the distal part 9 and merges the broader proximal part 8 into the narrower distal part 9. The transition piece 10 is designed matching the form-fit component 14. A coupling element 17, arranged in the distal part 9, is coupled to carriers 16 of the front grip element 5. The carriers 16 engage in an arc-shaped recess 11 of the distal part 9 of the guide groove 6. When the front grip element 5 and the rear grip element 4 are swiveled away from each other, the slide element 3 is moved along the guide element 2 to the proximal end. Moreover, the profile web 23 is pushed in the direction of the mounting opening 22'. When the safety device 15 is in a safety position in which it engages with the form-fit component 14 in the proximal part 8 of the guide groove 6, the transition piece 10 is pressed onto the form-fit component 14. As a result of the transition piece 10 being designed matching the form-fit component 14, the transition piece 10, in combination with the proximal part 8 of the guide groove 6, encloses the form-fit component 14. No play for movement of the form-fit component 14 remains, such that a bending or twisting of the form-fit component 14 is not possible. Moreover, the safety device 15 also cannot be displaced, such that the securing of the slide element 3 remains ensured, since the profile web 23 cannot be arranged in the mounting opening 22'.

The safety device 15 has a restoring spring 18, which presses the safety device 15 into the safety position. The safety device 15 is thus automatically transferred to the safety position as soon as there is no force acting on it. This ensures that the safety position is left only when the safety device 15 is actuated.

In a second embodiment of the invention, the sliding shaft instrument 1 has a rotation safety element 20 instead of the safety device 15. The rotation safety element 20 is arranged on a rotatable pin stub 21, which is axially displaceable. The pin stub 21 is arranged in a recess 31 of the bushing 26. The bushing 26 is fixedly connected to the grip part 5. The rotation safety element 20 has a form-fit element 35, which is arranged with a form fit on the guide element 2 when the grip parts 4, 5 are opened. This avoids too large an opening angle between the grip parts 4, 5. Moreover, the rotation safety element 20 has a protruding locking component 24, which is arranged in a recess 27 of the bushing 26 when the rotation safety element 20 is rotated to the safety position. The recess 27 of the bushing 26 has a shape matching the locking component 24. Moreover, the bushing 26 has an edge 30. The edge 30 encircles a part of the recess 31. The edge 30 extends axially away from the bushing 26. Moreover, the edge 30 has an arc-shaped configuration, i.e. it does not enclose the complete circle. A form-fit surface 28, 29 is arranged at the ends of the arc-shaped edge 30. The edge 30 engages in a recess 25 of the rotation safety element 20. The recess 25 is arranged in an arc shape around the pin stub 21. It begins and ends on a web 36, which is arranged on the locking component 24. The side faces of the recess 25 that are arranged on the web 36 have form-fit surfaces 37, 38.

The pin stub 21 is coupled to the bushing 26 via a spring 33. One end of the spring 33 is fixedly connected to the pin stub 21 by means of a holding element 32 arranged on the pin stub 21. The other end of the spring 33 is fixedly connected to the bushing 26 by another holding element 34 in the recess 31. The spring 33 pulls the pin stub 21 into the bushing 26.

In order to turn the rotation safety element 20, it first of all has to be pulled in the axial direction out of the bushing 26. In doing so, the spring force of the spring 33 has to be overcome, and the locking component 24 is also removed from the recess 27. By means of a rotation, the form-fit element 35 is rotated away from the guide element 2. The rotation of the rotation safety element 20 is blocked by the contact of the form-fit surface 28 of the edge 30 and of the form-fit surface 38 of the recess 25, or the form-fit surface 29 of the edge 30 and the form-fit surface 37 of the recess 25. A further rotation is not possible. The edge 31 encloses an angle which is such that the rotation safety element 20 can be rotated only through 90° from the safety position. It is thus not possible to rotate the form-fit element 35 in a direction away from the guide element 2. The opening angle of the grip part 4, 5 can thus be limited only by rotating the form-fit component 35 in to the guide element 2.

The spring 33 has the effect that the rotation safety element 20 can be pulled out of the safety position only when a force is applied from outside. If no force from outside is present, the rotation safety element 20 remains in the safety position. This increases the safety of the locking.

In both embodiments, the grip elements 4, 5 can be designed like scissor grips or like the grip elements 4', 5' of forceps. Moreover, spring elements 18, 19 can be provided on the grip parts 4', 5' in order to bring about an automatic opening of the grip parts 4', 5' after an actuation. Moreover, different jaw elements 12, 13 can be provided on the sliding shaft instrument 1. Thus, the jaw elements 12, 13 can consist of blades. In another embodiment, the jaw elements 12, 13 can be designed as punches 12', 13'.

The invention claimed is:

1. A dismantlable surgical sliding shaft instrument, comprising:
   a function shaft comprising a guide element, a slide element, an undercut rail and a profile web, the slide element mounted slidably on the guide element and comprising a coupling element, the undercut rail oriented along the sliding direction of the slide element and comprising a mounting opening at its proximal end, and the profile web comprising a profile that matches the rail,
   a grip part comprising a rear grip element and a front grip element, the rear grip element arranged at an angle at an end of the guide element, and the front grip element mounted pivotably on the guide element and comprising a carrier element configured to carry along the coupling element, and
   a safety device arranged on the rear grip element, the safety device engaging with a form-fit component in a proximal part of a guide groove in a safety position, wherein a transition piece matching the form-fit component is arranged between a distal part of the guide groove and the proximal part of the guide groove.

2. The sliding shaft instrument of claim 1, wherein the transition piece is configured at a right angle.

3. The sliding shaft instrument of claim 1, wherein the transition piece is integral with the slide element.

4. The sliding shaft instrument of claim 1, wherein the safety device comprises a restoring spring.

5. A dismantlable surgical sliding shaft instrument, comprising:
   a function shaft comprising a guide element, a slide element, an undercut rail and a profile web, the slide element mounted slidably on the guide element and comprising a coupling element, the undercut rail oriented along the sliding direction of the slide element and comprising a mounting opening at its proximal end, and the profile web comprising a profile that matches the rail,
   a grip part comprising a rear grip element and a front grip element the rear grip element arranged at an angle at an end of the guide element, and the front grip element mounted pivotably on the guide element and comprising a carrier element configured to carry along the coupling element, and
   a rotation safety element mounted on a rotatable pin stub and comprising a locking component, the pin stub mounted in a bushing secured in a rotationally fixed manner on the grip part, and the rotation safety element being arranged with a form fit on the function shaft in a safety position,
   wherein the bushing comprises an edge with a first form-fit surface and the rotation safety element comprises a recess with a second form-fit surface, the edge engages in the recess, and the second form-fit surface is arranged with a form fit on the first form-fit surface in an opening position of the rotation safety element.

6. The sliding shaft instrument of claim 5, wherein the edge has a third form-fit surface, the recess has a fourth form-fit surface, and the fourth form-fit surface is arranged with a form fit on the third form-fit surface in a second opening position of the rotation safety element.

7. The sliding shaft instrument of claim 6, wherein the first form-fit surface is arranged mirror-symmetrically with respect to the third form-fit surface and the second form-fit surface is arranged mirror-symmetrically with respect to the fourth form-fit surface.

8. The sliding shaft instrument of claim 6, wherein the edge is configured such that, in each opening position, the rotation safety element is rotated through a maximum of 90° from the safety position.

9. The sliding shaft instrument of claim 5, wherein the pin stub is axially displaceable, the bushing comprises a recess matching the locking component, and the rotation safety element is arranged in a safety position with the locking component in the recess of the bushing.

10. The sliding shaft instrument of claim 9, wherein the pin stub is coupled to the bushing by a spring.

* * * * *